United States Patent [19]
Del Rossi et al.

[11] Patent Number: 5,120,897
[45] Date of Patent: Jun. 9, 1992

[54] ISOPARAFFIN/OLEFIN ALKYLATION

[75] Inventors: Kenneth J. Del Rossi, Woodbury; Francis P. Ragonese, Cherry Hill; Jorge L. Soto, Sewell, all of N.J.

[73] Assignee: Mobil Oil Corporation, Fairfax, Va.

[21] Appl. No.: 569,310

[22] Filed: Aug. 20, 1990

[51] Int. Cl.$^5$ .............................................. C07C 2/60
[52] U.S. Cl. ..................... 585/726; 585/719; 585/721; 585/830; 585/833; 502/20; 502/514; 502/515
[58] Field of Search ............... 585/709, 710, 713, 726, 585/727, 729, 803, 830, 823, 833, 826, 827; 502/20, 514, 515

[56] References Cited

U.S. PATENT DOCUMENTS

| | | | |
|---|---|---|---|
| 2,333,648 | 11/1943 | Grosse et al. | 585/823 |
| 2,395,022 | 2/1946 | Sutton et al. | 585/823 |
| 2,804,491 | 8/1957 | May et al. | 260/683.4 |
| 3,251,897 | 5/1966 | Wise | 260/671 |
| 3,450,644 | 6/1969 | Lanewala et al. | 252/416 |
| 3,467,728 | 9/1969 | Hervert | 260/683.2 |
| 3,549,557 | 12/1970 | Bolton et al. | 252/455 |
| 3,624,173 | 11/1971 | Kirsch et al. | 260/671 |
| 3,644,565 | 2/1972 | Biale | 263/683.43 |
| 3,647,916 | 3/1972 | Caesar et al. | 260/683.43 |
| 3,655,813 | 4/1972 | Kirsch et al. | 260/683.43 |
| 3,706,814 | 12/1972 | Kirsch et al. | 260/683.43 |
| 3,738,977 | 6/1973 | Biale | 260/94.9 |
| 3,800,003 | 3/1974 | Sobel | 260/683.49 |
| 3,840,613 | 10/1974 | Eberly, Jr. et al. | 260/683.43 |
| 3,855,342 | 12/1974 | Huang et al. | 260/683.44 |
| 3,862,258 | 1/1975 | Huang | 260/683.44 |
| 3,893,942 | 7/1975 | Yang | 252/411 |
| 3,917,738 | 11/1975 | Fenske et al. | 260/683.43 |
| 3,997,621 | 12/1976 | Brennan | 260/683.15 B |
| 4,144,280 | 3/1979 | Winter, III | 585/464 |
| 4,308,414 | 12/1981 | Madgavkar et al. | 585/525 |
| 4,365,105 | 12/1982 | Morganson et al. | 585/525 |
| 4,384,161 | 5/1983 | Huang | 585/722 |
| 4,384,162 | 5/1983 | Vogel et al. | 585/830 |
| 4,429,177 | 1/1984 | Morganson et al. | 585/525 |
| 4,433,197 | 2/1984 | Vogel et al. | 585/472 |
| 4,454,366 | 6/1984 | Vogel et al. | 585/472 |
| 4,503,277 | 3/1985 | Himes | 585/464 |
| 4,918,255 | 4/1990 | Chou et al. | 585/331 |
| 4,935,577 | 6/1990 | Huss, Jr. et al. | 585/728 |
| 4,956,518 | 9/1990 | Child et al. | 585/728 |

OTHER PUBLICATIONS

Madgavkar, A. M., and Harold E. Swift, "Fixed-Bed Catalytic Process to Produce Synthetic Lubricants from Decene-1", Ind. Eng. Chem. Prod. Res. Dev., 22 (1983).

Kirsch, F. W. and John D. Potts, "Continuous Isobutane-Butene Alkylation with Zeolite Catalysts", ACS Div. Petrol. Chem. Preprints, 15, #3 (1970).

*Primary Examiner*—Anthony McFarlane
*Attorney, Agent, or Firm*—Alexander J. McKillop; Charles J. Speciale; Robert B. Furr, Jr.

[57] ABSTRACT

The present invention provides a Lewis acid-catalyzed isoparaffin/olefin alkylation process in which acid consumption and energy costs are decreased by employing an acid sorption stage to separate the Lewis acid catalyst from the alkylate product stream, or from a selected fraction of the alkylate product stream, and desorbing the Lewis acid from the sorption stage with an isoparaffin-containing alkylation process feedstream.

17 Claims, 2 Drawing Sheets

ISOPARAFFIN/OLEFIN ALKYLATION

FIELD OF THE INVENTION

The present invention relates to the art of improving the octane rating of gasoline by alkylating an isoparaffin with an; olefin stream in the presence of a Lewis acid-promoted catalyst to provide an alkylate product useful as a high octane blending component in gasoline.

BACKGROUND OF THE INVENTION

This invention results from a need to improve octane ratings for gasoline. Isoparaffin-olefin alkylation is a means to produce highly branched paraffins which effects this octane improvement.

Alkylation is a reaction in which an alkyl group is added to an organic molecule. Thus, an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This is a very valuable blending component in the manufacture of gasolines because of its high octane rating.

Traditionally, the process in the industry includes the use of hydrofluoric acid or sulfuric acid and a catalysis carried out under controlled temperature conditions. Low temperatures are utilized in the sulfuric acid process to minimize the side reaction of olefin polymerization and the acid strength is generally maintained at 88 to 94% by the continuous addition of fresh acid and the continuous withdrawal of spent acid. The hydrofluoric acid process is less temperature-sensitive and the acid is easily recovered and purified.

The typical types of alkylation currently used to produce high octane blending components, that is, the hydrofluoric acid and sulfuric acid alkylation processes, have inherent drawbacks including environmental concerns, acid consumption and sludge disposal. With the increasing demands for octane and the increasing environmental concerns, it has been desirable to develop an alkylation process based on a catalyst system which can meet product quality demands, while at the same time minimizing safety and environmental problems. Studies to date indicate that Lewis acid-catalyzed alkylation processes have the potential to meet the refiners' requirements for alkylate octane and volumetric production. Examples of Lewis acids include $BF_3$, $AlCl_3$ and $SbF_5$, of which $BF_3$ presently appears to be most promising to catalyze industrial isoparaffin:olefin alkylation. The following references provide an overview of art related to $BF_3$-catalyzed isoparaffin-olefin alkylation.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as water-forming compound.

U.S. Pat. No. 3,450,644 discloses a method for regenerating a zeolite catalyst used in hydrocarbon conversion processes involving carbonium ion intermediates.

U.S. Pat. No. 3,549,557 describes alkylation of isobutane with $C_2$–$C_3$ olefins using certain crystalline aluminosilicate zeolite catalysts in a fixed-, moving- or fluidized-bed system.

U.S. Pat. No. 3,644,565 discloses alkylation of a paraffin with an olefin in the presence of a catalyst comprising a Group VIII noble metal present on a crystalline aluminosilicate zeolite. The catalyst is pretreated with hydrogen to promote selectivity.

U.S. Pat. No. 3,647,916 describes an isoparaffin-olefin alkylation process featuring use of an ion-exchanged crystalline aluminosilicate, isoparaffin/olefin molar ratios below 3:1 and regeneration of the catalyst.

U.S. Pat. No. 3,655,813 discloses a process for alkylating $C_4$–$C_5$ isoparaffins with $C_3$–$C_9$ olefins using a crystalline aluminosilicate zeolite catalyst wherein a halide adjuvant is used in the alkylation reactor. The isoparaffin and olefin are introduced into the alkylation reactor at specified concentrations and catalyst is continuously regenerated outside the alkylation reactor.

U.S. Pat. No. 3,706,814 discloses another zeolite-catalyzed isoparaffin-olefin alkylation process and further provides for the addition of $C_5+$ paraffins such as Udex raffinate or $C_5+$olefins to the alkylation reactor feed and the use of specific reactant proportions, halide adjuvants, etc.

U.S. Pat. No. 3,840,613 discloses a process for alkylation of paraffin hydrocarbons with olefins by reaction in the presence of a crystalline aluminosilicate zeolite catalyst activated by the sequential steps of ion exchange, steaming, reexchange and calcination.

U.S. Pat. No. 3,624,173 discloses an isoparaffin-olefin alkylation which uses crystalline aluminosilicate zeolites containing gallium.

U.S Pat. No. 3,738,977 discloses alkylation of paraffins with ethylene using a zeolite catalyst which possesses a Group VII metal component. The catalyst is pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone. Thereafter, the reactants are passed concurrently with the catalyst so that a controlled amount of olefin is adsorbed into the catalyst before the combination of reactants and catalyst is introduced into an alkylation zone. This controlled olefin adsorption is thought to prevent polymerization of the olefin during alkyation.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large-pore zeolite with a Lewis acid is reported to increase the activity and selectivity of the zeolite, thereby effecting alkylation with high olefin space velocity and low isoparaffin/olefin ratio.

The article entitled "Fixed Bed Catalytic Process to Product Synthetic Lubricants from Decene-1", *Ind. Eng. Chem. Prod. Res. Dev.*, 22, (1983), teaches oligomerizing olefins to produce fluids with lubricating properties using a silica-$BF_3$-water catalyst The authors further teach that with this system much of the $BF_3$ can be recycled to minimize $BF_3$ consumption and disposal problems The reference teaches that water is a necessary component of the system and that in its absence a $BF_3$-silica catalyst rapidly deactivates. The reference further teaches that for less reactive olefins, such as decene-1, a useful degree of oligomerization is achieved only by adding a measurable quantity of an activator such as water or a primary alcohol to $BF_3$. The authors further point out that other $BF_3$ activators, such as ethers, ketones, acids and anhydrides, are also effective olefin oligomerization catalysts A commercialized process is reported wherein alkylation of benzene with ethylene, propylene or butenes is achieved by using a $BF_3$-alumina catalyst with BF continually added to the feedstock. The article states that the process minimizes both $BF_3$ consumption and disposal problems and further provides a product having excellent lubricating properties. The catalyst is said to require water as an activator.

In U.S. Pat. No. 4,308,414 an olefin, such as 1-decene, is oligomerized in the presence of a three-component catalyst comprising boron trichloride, a minute amount of water and a particulate absorbent material such as silica to a lubricating product predominating in those oligomer fractions having viscosities within the lubricating oil range such as the trimer and tetramer.

U.S. Pat. No. 4,429,177 further relates to a method for making lubricating oil utilizing a catalyst comprising boron trifluoride, a minute amount of elemental oxygen and a particulate absorbent material such as silica. The reference points out that the two-component catalyst comprising a solid absorbent and boron trifluoride gradually loses activity after a period of continued use, which aging cannot be conveniently corrected by increasing the boron trifluoride pressure. As a solution, the reference teaches that this aging can be essentially prevented if a minute amount of elemental oxygen is fed to the reactor.

U.S. Pat. No. 3,997,621 relates to oligomerization of olefins catalyzed by boron trifluoride which is controlled to yield desired trimer as a dominant lubricant product by adding small amounts of ester together with water or alcohol promoter.

U.S. Pat. No. 4,365,105 also relates to oligomerizing an olefin to form lubricating oils in the presence of three-component catalyst which comprises a particular silica absorbent with boron trifluoride and water absorbed on the silica.

U.S. Pat. No. 2,804,491 relates to an isoparaffin/olefin alkylation to make gasoline at temperatures between -20 and 150° F. utilizing a two-component catalyst comprising essentially excess $BF_3$ with a "silica stabilized gel alumina". No activators are taught.

In the past, severe activity and stability problems have been noted with respect to zeolite based systems. U.S. Pat. Nos. 3,251,902 and 3,893,942, as well as French Patent 1,593,716, and the article by Kirsh and Potts, *Div. of Pet. Chem. A.C.S.* 15, A109 (1970), exemplify these problems. Improved stability was noted when a Lewis acid such as $BF_3$ was used in combination with macroreticular acid cation exchange resins as pointed out in U.S. Pat. No. 3,855,342. More recently, U.S. Pat. No. 4,384,161 has disclosed the use of BF in combination with large pore zeolites such as ZSM-4 and Beta to effectively catalyze isoparaffin/olefin alkylation reactions.

U.S. Pat. No. 3,467,728 relates to a process for isomerizing olefinic hydrocarbon, such as 1-butene or 1-pentene, by contacting the hydrocarbon with a catalyst comprising a crystalline alumina silicate combined with a substantially anhydrous boron halide.

U.S. Pat. No. 3,800,003 relates to a process for producing an alkylation reaction product from an isoparaffinic reactant and an olefinic reactant containing 1-butene, 2-butene and isobutene which includes passing the olefinic reactant through an isomerization zone. The isomerization catalyst comprises a crystalline aluminosilicate combined with a substantially anhydrous boron halide which can be boron trifluoride. Conventional catalysts are utilized for the alkylation reaction and include sulfuric acid and hydrogen fluoride catalyst which have the disadvantages set forth above.

The problem of acid consumption remains as an obstacle to commercialization of Lewis acid catalyzed alkylation, first because of the high cost of suitable Lewis acids, and second because of the cost of disposing of an acid neutralization byproduct if the acid is not recycled. Specifically, it would be highly beneficial to provide a process which efficiently separates and recycles the Lewis acid component of the alkylation catalyst to the alkylation reaction zone while avoiding the capital and operating costs associated with a Lewis acid/light aliphatic fractionation section. For example, in a typical $BF_3$-catalyzed isobutane:2-butene alkylation process employing feeds contianing minor amounts of lighter hydrocarbons, the reactor effluent product is first fractionated to separate $C_4-$ components from $C_5+$ alkylate. The overhead stream from this fractionation step typically contains not only $BF_3$ but also unreacted propane which must be removed before the $BF_3$ is recycled to the alkylation reactor. While the two components are separable by distillation, their close boiling points require a tall, expensive distillation tower. Further, the tower must be constructed with a nickel-rich alloy such as Monel to resist corrosive attack by the $BF_3$.

U.S. Pat. No. 4,384,162 to Vogel teaches a method of removing $BF_3$ from organic liquids by passing the organic liquid through a bed of granular polyvinyl alcohol (PVA). When the PVA adsorbent is saturated with $BF_3$, it is taken out of service for extraction of $BF_3$ from the PVA. This $BF_3$ recovery step is accomplished by heating the PVA to a temperature of about 100° C. to vaporize off the $BF_3$, or alternatively, contacting the PVA with a polar solvent to desorb $BF_3$. Unfortunately, neither of these regeneration techniques lends itself to continuous $BF_3$ recovery in conjunction with a $BF_3$ alkylation process. Heating the sorbent to vaporize $BF_3$ necessarily requires handling a recycle stream enriched in $BF_3$, an option complicated by numerous environmental and safety precautions. On the other hand, while dissolving the $BF_3$ from the PVA with a polar solvent would seem to eliminate the safety and environmental hazards associated with handling a gaseous $BF_3$ stream, the $BF_3$ must be separated from the polar solvent before recycling $BF_3$ to the alkylation reaction zone. Thus, it would be highly beneficial if a Lewis acid sorption process could be developed which could be readily integrated into a continuous alkylation scheme without the hazards associated with handling purified Lewis acids.

The alkylate gasoline produced by the processes discussed above is not only characteristically free from impurities such as sulfur, but is also low in aromatics. With the advent of increasingly stringent regulations restricting the content of motor gasolines, demand for such alkylate gasolines will continue to increase. To meet the market requirements for alkylate gasoline octane quality while promoting safe refinery operation and minimizing environmental risks, it would be highly desirable to provide a Lewis acid catalyzed isoparaffin-olefin alkylation process for the production of motor gasoline blending stock which process minimizes Lewis acid catalyst consumption by recovering and recycling the Lewis acid catalyst from the product stream without handling concentrated Lewis acid, and without the capital and operating costs associated with Lewis acid/$C_3-$ hydrocarbon distillation.

Each of the preceeding references is incorporated by reference as if set forth at length herein

SUMMARY OF THE INVENTION

The present invention provides an isoparaffin/olefin alkylation process conducted in the presence of a catalyst complex comprising a Lewis acid in which acid consumption and energy costs are decreased by employing an acid sorption stage to separate the Lewis acid component of the catalyst complex from the alkylate product stream, or from a selected fraction of the alkylate product stream. The invention further promotes safe refinery operation and minimizes environmental risks associated with handling concentrated Lewis acids by desorbing and recycling dilute recycled Lewis acid with an isoparaffin-containing feedstream.

The invention therefore includes, in a first process aspect, a process for alkylating an isoparaffin with an olefin comprising the steps of:

(a) contacting an isoparaffin having from 4 to 8 carbon atoms with an olefin having from 2 to 12 carbon atoms in the liquid state in an alkylation reaction zone at temperature from about $-40°$ C. to about 200° C. with an alkylation catalyst complex comprising boron trifluoride, wherein the molar ratio of said isoparaffin to said olefin is from about 1:1 to about 100:1 to evolve a product stream containing $C_5+$ alkylate;

(b) separating said product stream of step (a) into a first stream containing $C_3-$ hydrocarbons and Lewis acid and a second stream enriched in $C_5+$ alkylate;

(c) providing a sorbent having a controlled affinity for said Lewis acid;

(d) contacting said first stream of step (b) with said sorbent to sorb said Lewis acid;

(e) discontinuing flow of said first stream to said sorbent of step (d);

(f) desorbing sorbed Lewis acid from said sorbent by flowing an isoparaffin having from 4 to 8 carbon atoms in contact with said sorbent to form an isoparaffin stream enriched in said Lewis acid; and (g) flowing said Lewis acid-enriched stream of step (f) to said alkylation reaction zone of step (a).

The invention provides, in a second process aspect, a continuous isoparaffin-olefin alkylation process comprising the steps of:

(a) contacting an isoparaffin having from 4 to 8 carbon atoms with an olefin having from 2 to 12 carbon atoms in the liquid state in an alkylation reaction zone at temperature from about $-20°$ C. to about 200° C. with an alkylation catalyst complex comprising a Lewis acid, wherein the molar ratio of said isoparaffin to said olefin is from about 2 to about 50 to evolve a product stream containing $C_5+$ alkylate;

(b) separating said product stream of step (a) into a first stream containing $C_3-$ hydrocarbons and Lewis acid and a second stream enriched in $C_5+$ alkylate;

(c) providing first and second sorption zones containing sorbent having a controlled affinity for said Lewis acid;

(d) contacting said first stream of step (b) with said sorbent in said first sorption zone to sorb said Lewis acid;

(e) interrupting flow of said first stream of step (b) to said first sorption zone;

(f) contacting said first stream of step (b) with sorbent in said second sorption zone to sorb said Lewis acid;

(g) desorbing sorbed Lewis acid from said sorbent of said first sorption zone by flowing an isoparaffin having from 4 to 8 carbon atoms in contact with said sorbent of said first sorption zone to form an isoparaffin stream enriched in said Lewis acid;

(h) flowing said Lewis acid-enriched stream of step (g) to said alkylation reaction zone of step (a).

(i) interrupting flow of said first stream of step (b) to said second sorption zone;

(j) contacting said first stream of step (b) with sorbent in said first sorption zone to sorb said Lewis acid;

(k) desorbing sorbed Lewis acid from said sorbent in said second sorption zone by flowing an isoparaffin having from 4 to 8 carbon atoms in contact with said sorbent of said second sorption zone to form an isoparaffin stream enriched in said Lewis acid;

(l) flowing said Lewis acid-enriched stream of step (k) to said alkylation reaction zone of step (a);

(m) interrupting flow of said first stream of step (b) to said second sorption zone; and (n) repeating steps (d) through (m) to continuously recover said Lewis acid from said first stream and to recycle said recovered Lewis acid to said alkylation reaction zone of step (a).

DETAILED DESCRIPTION

Alkylate is a particularly valuable portion of the gasoline pool, as it has both high research and motor octane, contains no olefins or aromatics and little or no sulfur, demonstrates excellent stability, and is clean burning. The present process, therefore, not only produces a superior motor fuel blending component, but also improves refinery safety and reliability while minimizing environmental concerns historically associated with the manufacture of alkylate gasolines.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, 3-methylhexane, 2-methylbutane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these C olefins, with butene-2 being the most preferred. Suitable feedstocks for the process of the present invention are described in U.S. Pat. No. 3,862,258 to Huang et al. at column 3, lines 44-56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 10:1.

Process Conditions

The present alkylation process is suitably conducted at temperatures of from about −40° to about 500° C., preferably from about −40° to about 200° C., and more preferably below about 150° C. to avoid undesirable side reactions. Lower reaction temperatures are preferred to maximize alkylate octane. The upper temperature limit is more critical when the process is conducted in the presence of a resin catalyst as described below. Lower temperatures are generally preferred, for example temperatures as low as −20° C. may be effectively employed. Operating temperature typically falls within the range of about −20° to about 60° C., with the most preferred operating temperatures falling within the range of about −20° to about 20° C.

Operating pressure is controlled to maintain the reactants in the liquid phase, and is suitably from about 50 to about 1500 psig, preferably from about 100 to about 500 psig. The catalyst weight hourly space velocity as well as the Lewis acid dosage varies with the particular composite catalyst system employed.

The particular operating conditions used in the present process will depend on the specific alkylation reaction being effected. Process conditions such as temperature, pressure, space velocity and molar ratio of the reactants will affect the characteristics of the resulting alkylate, and may be adjusted within the disclosed ranges by those skilled in the art with only minimal trial and error.

Catalysts

The catalyst complex useful in the present invention may comprise either a solid or a liquid catalyst promoted by a Lewis acid.

Suitable solid catalyst systems include a Lewis acid with at least one selected from the group consisting of a macrorectiular ion exchange resin, a large-pore zeolite, and a nonzeolitic solid. A Lewis acid is generally considered to be a molecule which is capable of combining with another molecule or ion by forming a covalent chemical bond with two electrons from the second molecule or ion; that is, the Lewis acid is an electron acceptor. Examples of Lewis acids include boron trifluoride ($BF_3$), boron trichloride ($BCl_3$), antimony pentafluoride ($SbF_5$), and aluminum chloride ($AlCl_3$). The present invention contemplates the use of all Lewis acids as those set forth in *Friedel-Crafts and Related Reactions*, Interscience Publishers, Chapters III and IV (1963), which is incorporated herein by reference.

The non-zeolitic inorganic oxide of the solid catalyst may be selected from among the diverse inorganic oxides, examples of which include, but are not limited to, alumina, silica, boria, oxides of phorphorus, titanium dioxide, zirconium dioxide, chromia, zinc oxide, magnesia, calcium oxide, silica-alumina, silica-magnesia, silica-alumina-magnesia, silica-alumina-zirconia, as well as the naturally occurring inorganic oxides of various states of purity such as bauxite, clay, diatomaceous earth, merely to name a few. The preferred inorganic oxides are amorphous silicon dioxide and aluminum oxide. Isoparaffin/olefin alkylation in the presence of a non-zeolitic inorganic oxide and a Lewis acid is taught in U.S. Pat. No. 4,918,255 to Chou et al., as well as in allowed U.S. patent application Ser. No. 377,993, filed Jul. 11, 1989. The entire disclosures of both are incorporated herein by reference.

The large pore crystalline molecular sieves which can be used in the present invention include those which absorb 2,2,4-trimethylpentane. Representative large pore crystalline molecular sieves include, for example, the following zeolites: ZSM-3, ZSM-4, ZSM-12, ZSM-18, ZSM-20, zeolite L, mordenite, faujasite, zeolite Y, and the rare earth metal-containing forms of the above-listed zeolites. Zeolite Beta can also be used in the present invention, although it is understood that zeolite Beta may exhibit characteristics of a medium-pore zeolite or a large-pore zeolite depending upon process conditions. Isoparaffin/olefin alkylation in the presence of a large pore zeolite is taught in U.S. Pat. No. 4,918,255 to Chou et al., cited above, as well as in allowed U.S. patent application Ser. No. 425,497, filed Oct. 17, 1989, which is a Continuation of Ser. No. 219,130, filed Jul. 15, 1988, now abandoned.

The large pore zeolite selected for use in the present alkylation process generally exhibits an Alpha value over a wide range of from less than about 1 to more than 1000. The index "Alpha value" measures zeolite acidic functionally and is described in detail in 61 *J. Catalysis* 395 (1980), which description is incorporated by reference as if set forth at length herein.

Zeolites of low acidity, i.e. zeolites having alpha values of less than about 200, can be achieved by a variety of techniques including (a) synthesizing a zeolite with a high silica:alumina ratio, (b) steaming, (c) steaming followed by dealuminization, and (d) substituting framework aluminum with other species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures using elevated pressure, e.g. at from about 350° to about 750° F. with pressure of from about 10 to about 200 atmospheres. Specific details of several steaming procedures may are disclosed in U.S. Pat. Nos. 4,325,994; 4,374,296; and 4,418,235, which patents are incorporated as if set forth at length herein. In addition to, or apart from these steaming procedures, the surface acidity of the zeolite an be eliminated or reduced by treatment with bulky reagents as described in U.S. Pat. No. 4,520,221, which patent is incorporated herein by reference.

Additional molecular sieves which find utility in conjunction with the present invention include pillared and/or clays; aluminophosphates, e.g. ALPO-5, VPI-5; silicates and/or clays; aluminophosphates, e.g. ALPO-5, VPI-5; silicoaluminophosphates, e.g. SAPO-5, SAPO-37, SAPO-31, SAPO-40, SAPO-41; and other metal aluminophosphates. These are variously described in U.S. Patents 4,440,871; 4,554,143; 4,567,029; 4,666,875; and 4,742,033.

The macroreticular acid cation exchange resins useful in the present invention are characterized by substantial porosity, high surface area, and a low surface acid concentration, generally less than about 0.5 milliequivalents of hydrogen ion per square meter surface area. The cation exchange resin can contain a small amount of water, generally from about 0.5 to about 20 percent by weight. The macroreticular resins utilized in the process of this invention are characterized by the presence of acid functional groups and a structure having a high degree of true porosity while possessing rigidity and being subject to minimum volume change when immersed or removed from solvents or solutions.

The macroreticular acid ion exchange resin used is typified by the presence of sulfonic acid groups, e.g. the sulfonated styrene-divinylbenzene copolymer exchange resins such as those commercially available as Amberlyst-15, Amerlyst XN-1005, Amberlyst XN-1010, Amberlyst XN-1011, Amberlyst XN-1008, and Amberlite 200. The properties of these resins are set forth in U.S. Pat. No. 3,862,258 to Huang et al., the disclosure of which is incorporated herein by reference.

The amount of catalyst used in the present process can be varied over relatively wide limits. In general, the amount of catalyst as measured by the weight hourly space velocity of the olefin can range from about 0.01 to about 100. The amount of catalyst selected for a particular reaction will be determined by several variables including the reactants involved as well as the nature of the catalyst and the operating conditions used.

Sorbents

Sorbents suitable for use in the present process must preferentially sorb Lewis acids from hydrocarbon gas streams having such compounds dissolved therein, and retain the sorbed Lewis acid until the enriched sorbent is contacted with a lean stripping fluid. More specifically, the sorbent must preferentially sorb a Lewis acid from a hydrocarbon stream containing $C_3-$ components and subsequently permit the Lewis acid to be desorbed into a second hydrocarbon stream containing isoparaffins to regenerate the sorbent and to recycle Lewis acid diluted in the isoparaffin-containing hydrocarbon stream to the alkylation reactor.

Examples of such sorbents include both solid and liquid Lewis bases. Suitable Lewis bases which are normally solid under sorption conditions include calcium fluoride ($CaF_2$), as well as polyvinyl alcohol (PVA). Suitable Lewis bases which are normally liquid under sorption conditions include diethylether, dioxane and anisole.

Solid sorbents are preferably packed into fixed beds equipped with flow distributors to promote uniform contact with the solid sorbent. Lewis acid sorption by a liquid sorbent, on the other hand, may be carried out using various gas-liquid contacting means well known to those skilled in the art, for example, a tower containing trays or packing to improve liquid-vapor contact. The enriched sorbent is then stripped of Lewis acid by gas-liquid stripping of the sorbent liquid with an isoparaffin-containing alkylation feedstream. For a general survey of suitable vapor-liquid contacting techniques and process equipment, see A. L. Kohl, "Absorption and Stripping", HANDBOOK OF SEPARATION TECHNOLOGY, 340 (1987).

Process Flow

Figure 1:
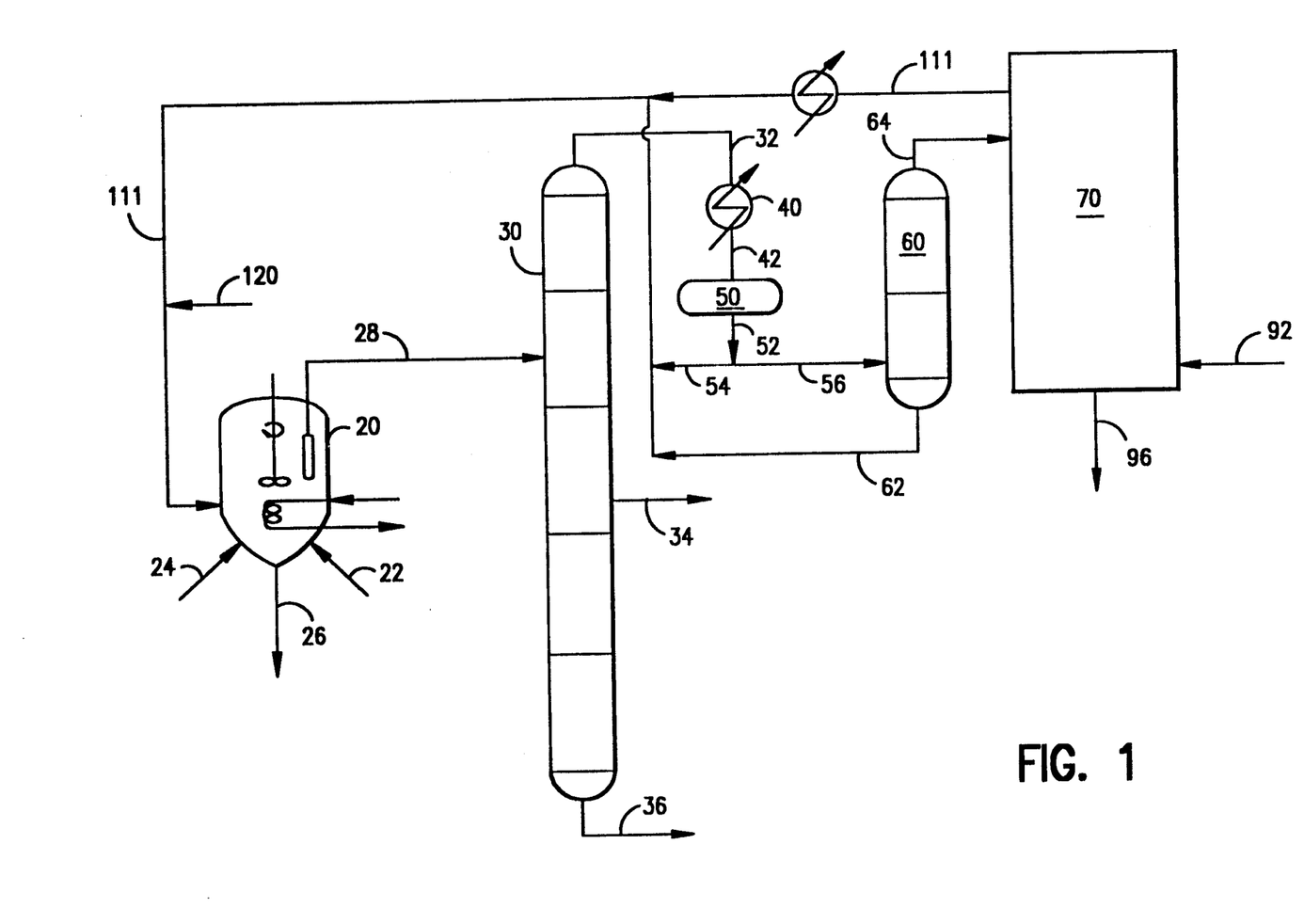
FIG. 1 is a simplified schematic diagram showing the major processing steps of one embodiment of the present invention.
Figure 2:
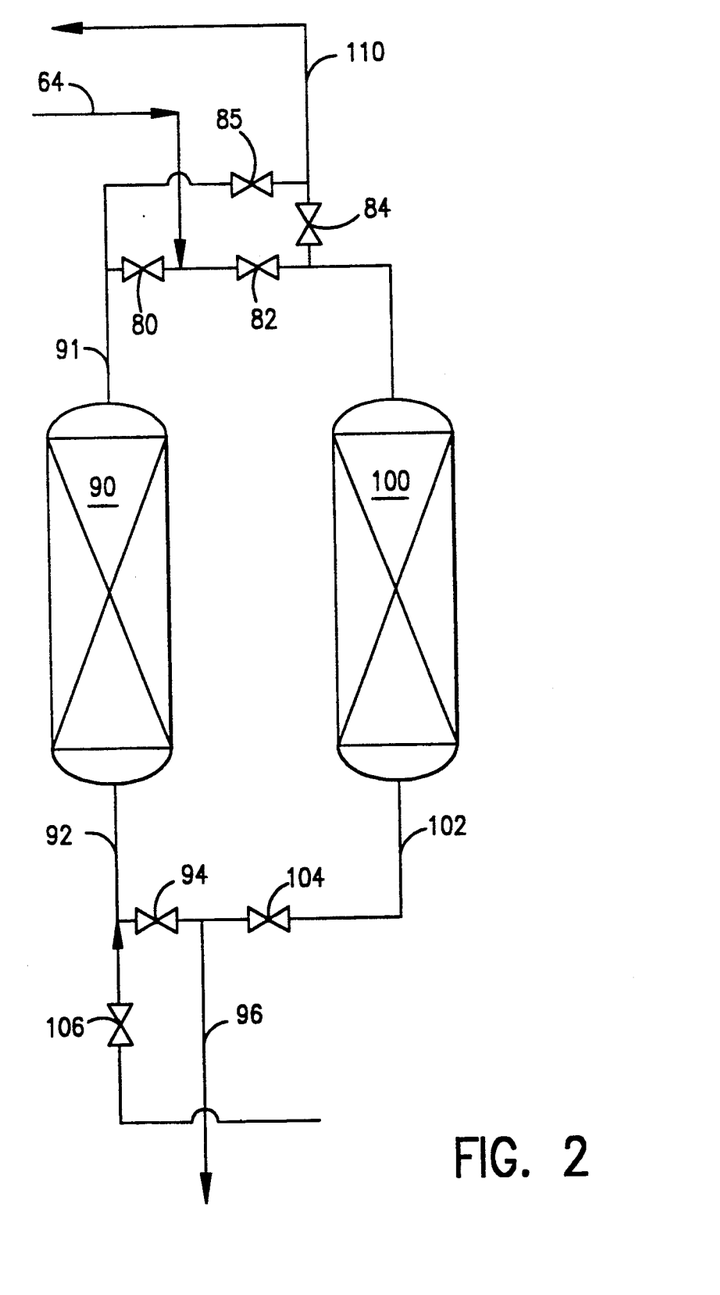
FIG. 2 schematically illustrates an embodiment of the sorption section of the present invention.

The Figures illustrate one embodiment of the present invention in which a continuous alkylation process is conducted in the presence of a catalyst complex comprising a Lewis acid and a solid catalyst in a stirred tank reactor containing a slurry of reactants and catalyst. Thus, while a stirred tank configuration is illustrated, it is to be understood that other suitable reactors may be employed, for example, tubular reactors. Referring now to FIG. 1, isoparaffin, e.g. isobutane, containing recycled $BF_3$ is mixed with makeup $BF_3$ from line 120 and charged through line 111 to stirred tank reactor 20. Butane feed and fresh catalyst are also added to the stirred tank reactor to provide an effective weight hourly space velocity (WHSV) of about 0.5 $hr^{-1}$. The total recycle and makeup $BF_3$ charge rate is controlled to maintain a concentration of $BF_3$ within the reactor which exceeds that which is necessary to saturate the zeolite, non-zeolitic inorganic oxide, or ion exchange resin which comprises the solid component of the selected catalyst complex.

Fresh catalyst is charged to stirred tank reactor 20 through line 22 to maintain the desired catalyst activity while olefin, e.g. butene, is charged to the stirred tank reactor via line 24. The relative flowrates of isoparaffin and olefin are controlled to maintain an isoparaffin:olefin ratio of about 10:1 within the stirred tank reactor. Spent catalyst is withdrawn from stirred tank reactor 20 through line 26 and may be recycled through regeneration facilities (not shown) or may be outhauled for suitable disposal.

Product is withdrawn from reactor 20 via line 28 and charged to separation means, for example distillation column 30 to separate $C_5+$ alkylate from n-butane, isobutane, and the Lewis acid promoter. The overhead product from distillation column 30, enriched in isobutane and the Lewis acid promoter, which is $BF_3$ in the present embodiment, is withdrawn from an upper section of the distillation column 30 through line 32 and at least partially condensed in overhead condenser 40. The condensate mixture from overhead condenser 40 flows through line 42 to accumulator 50. The accumulated condensate mixture flows from accumulator 50 through line 52 and is split between lines 54 and 56, which recycle isobutane to the reactor 20 and charge condensate mixture to depropanizer fractionator 60, respectively. The depropanizer bottom stream, enriched in isobutane, flows through line 62, and is recycled to reactor 20 through line 111 together with condensate mixture from line 54. Depropanizer overhead, enriched in $C_3-$ hydrocarbons and $BF_3$, flows through line 64 to a Lewis acid sorption section 70.

The sorption section may comprise one or more sorption zones, preferably at least two sorption zones piped in parallel to provide continuous swing operation. In the presently described embodiment, the sorbent comprises a solid Lewis base, for example, polyvinyl alcohol (PVA). Specifically, it is preferred to configure the sorption section to provide at least one sorption zone on stream while at least one sorption zone is being regenerated. In the present embodiment, the Lewis acid component of the catalyst complex comprises $BF_3$ and is recovered from the depropanizer overhead stream in a first sorption zone. $BF_3$ is stripped from the sorbent with fresh isobutane feed in a second sorption zone to recycle recovered $BF_3$ to the reactor 20. The fresh isobutane feed advantageously dilutes the desorbed $BF_3$ to enhance refinery safety and minimize environmental risks associated with handling a highly concentrated Lewis acid.

Referring now to FIG. 2, the depropanizer overhead stream is charged through line 64 through open valve 80 and line 91 to a first sorption zone 90 which contains a sorbent having an affinity for sorbing $BF_3$. The lean $C_3-$ stream is withdrawn from the first sorption zone 90 through line 92 and flows through open valve 94 and line 96 for upgrading in a downstream process (not shown), for fuel in the refinery fuel gas system, or for sale as liquified petroleum gas (LPG).

The first sorption zone sorbs $BF_3$ from the $C_3-$ hydrocarbon stream until the sorbent reaches complete saturation as evidenced by $BF_3$ breakthrough, or preferably at a predetermined level of saturation below that which permits substantial $BF_3$ breakthrough.

Flow of the $BF_3$-containing $C_3-$ hydrocarbon gas is then shifted to the second sorption zone 100 and the first sorption zone is regenerated by flowing isobutane through the sorption zone to desorb $BF_3$. Valves 80 and 84 are closed and valve 82 is opened to divert flow of $BF_3$-containing $C_3-$ hydrocarbon gas from the first sorption zone 90 to the second sorption zone 100. Lean $C_3-$ hydrocarbon gas stream is withdrawn from sorption zone 100 through line 102. Valve 94 is closed and valve 104 is opened to allow the lean $C_3-$ hydrocarbon gas stream to flow out of the sorption section as described above.

During the period of time when the $BF_3$ sorption duty is shifted to the second sorption zone, the first sorption zone is regenerated by flowing at least a portion of the isoparaffin, e.g. isobutane, charge stream in contact with the $BF_3$-enriched sorbent. The isobutane desorbs and recycles $BF_3$ to the reactor 20. Makeup $BF_3$ may be added to the isobutane effluent stream as required to maintain the desired $BF_3$ level in reactor 20.

Isobutane charge flows through line 92 and open valve 106 to contact the sorbent in the first sorption zone 90 where it becomes enriched with $BF_3$. The $BF_3$-enriched isobutane flows through line 91 and open valve 85 to reactor 20 through line 110. Makeup $BF_3$ is added to line 110 through line 120 upstream of reactor 20 as described above and shown in FIG. 1. When the second sorption zone 100 becomes saturated with $BF_3$, or at a predetermined point before saturation, the valving is reset to flow isobutane through the second sorption zone to desorb $BF_3$ from the sorbent while contacting the first, regenerated sorption zone with $BF_3$-enriched $C_3-$ hydrocarbon gas. Flow of $BF_3$-enriched $C_3-$ hydrocarbon gas and isobutane are alternated through the sorption zones as described above to provide continuous operation with one sorption zone removing $BF_3$ while another sorption zone is regenerated with isobutane charge. Thus two sorption zones piped and valved in parallel for swing operation as described are required for continuous operation, and three or more sorption zones are preferred to enable continuous operation while one sorption zone is out of service for extended maintenance.

Changes and modifications in the specifically described embodiments can be carried out without departing from the scope of the invention which is intended to be limited only by the scope of the appended claims.

We claim:

1. A process for alkylating an isoparaffin with an olefin comprising the steps of:
   (a) contacting an isoparaffin having from 4 to 8 carbon atoms with an olefin having from 2 to 12 carbon atoms in the liquid state in an alkylation reaction zone at temperature from about $-20°$ C. to about $150°$ C. with an alkylation catalyst complex comprising $BF_3$, wherein the molar ratio of said isoparaffin to said olefin is from about 2 to about 50 to evolve a product stream containing $C_5+$ alkylate;
   (b) separating said product stream of step (a) into a first stream enriched in $C_4-$ hydrocarbons and $BF_3$ and a second stream enriched in $C_5+$ alkylate;
   (c) providing a sorbent having a controlled affinity for said $BF_3$;
   (d) contacting said first stream of step (b) with said sorbent to sorb said $BF_3$;
   (e) discontinuing flow of said first stream to said sorbent of step (d);
   (f) desorbing sorbed $BF_3$ from said sorbent by flowing an isoparaffin having from 4 to 8 carbon atoms in contact with said sorbent to form an isoparaffin stream enriched in said $BF_3$; and
   (g) flowing said $BF_3$-enriched isoparaffin stream of step (F) to said alkylation reaction zone of step (a).

2. The process of claim 1 wherein said alkylation catalyst complex further comprises a non-zeolitic solid.

3. The process of claim 1 wherein said alkylation catalyst complex further comprises a zeolite.

4. The process of claim 3 wherein said alkylation catalyst complex further comprises a zeolite having a Constraint Index of less than about 1.

5. The process of claim 1 wherein said alkylation catalyst complex comprises a macroreticular ion-exchange resin.

6. The process of claim 1 wherein said sorbent comprises $CaF_2$ on an activated carbon support.

7. The process of claim 1 wherein said sorbent comprises a Lewis base.

8. The process of claim 7 wherein said Lewis base comprises an oxygenate.

9. The process of claim 8 wherein said oxygenate comprises polyvinyl alcohol.

10. A continuous isoparaffin-olefin aliylation process comprising the steps of:
    (a) contacting an isoparaffin having from 4 to 8 carbon atoms with an olefin having from b 2 to 12 carbon atoms in the liquid state in an alkylation reaction zone at temperature from about $-20°$ C. to about $200°$ C. with an aliylation catalyst complex comprising $BF_3$, wherein the molar ratio of said isoparaffin to said olefin is from about 2 to about 50 to evolve a product stream containing $C_5+$ alkylate;
    (b) separating said product stream of step (a) into a first stream containing $C_3-$ hydrocarbons and $BF_3$ and a second stream enriched in $C_5+$ alkylate;
    (c) providing first and second sorption zones containing sorbent having a controlled affinity for said $BF_3$;
    (d) contacting said first stream of step (b) with said sorbent in said fist sorption zone to sorb said $BF_3$;
    (e) interrupting flow of said first stream of step (b) to said first sorption zone;
    (f) contacting said first stream of step (b) with sorbent in said second sorption zone to sorb said $BF_3$;
    (g) desorbing sorbed $BF_3$ from said sorbent of said first sorption zone by flowing an isoparaffin having from 4 to 8 carbon atoms in contact with said sorbent of said first sorption zone to form an isoparaffin stream enriched in said $BF_3$;
    (h) flowing said Lewis acid-enriched stream of step (g) to said alkylation reaction zone of step (a);
    (i) interrupting flow of said first stream of step (b) to said second sorption zone;

(j) contacting said first stream of step (b) with sorbent in said first sorption zone to sorb said $BF_3$;

(k) desorbing sorbed $BF_3$ from said sorbent in said second sorption zone by flowing an isoparaffin having from 4 to 8 carbon atoms in contact with said sorbent of said second sorption zone to form an isoparaffin stream enriched in said $BF_3$;

(l) flowing said $BF_3$-enriched stream of step (k) to said alkylation reaction zone of step (a);

(m) interrupting flow of said first stream of step (b) to said second sorption zone; and (n) repeating steps (d) through (m) to continuously recover said $BF_3$ from said first stream and to recycle said recovered $BF_3$ to said alkylation reaction zone of step (a).

11. The process of claim 10 wherein said alkylation catalyst complex further comprises a non-zeolitic solid.

12. The process of claim 10 wherein said alkylation catalyst complex further comprises a zeolite.

13. The process of claim 10 wherein said alkylation catalyst complex further comprises a zeolite having a Constraint Index of less than about 1.

14. The process of claim 10 wherein said alkylation catalyst complex comprises a macroreticular ion-exchange resin.

15. The process of claim 10 wherein said sorbent comprises a Lewis base.

16. The process of claim 10 wherein said sorbent comprises $CaF_2$ on an activated carbon support.

17. The process of claim 10 wherein said sorbent is a polyvinyl alcohol.

* * * * *

UNITED STATES PATENT AND TRADEMARK OFFICE
CERTIFICATE OF CORRECTION

PATENT NO. : 5,120,897
DATED : June 9, 1992
INVENTOR(S) : K. J. Del Rossi, F. P. Ragonese and J. L. Soto It is certified that error appears in the above-identified patent and that said Letters Patent is hereby corrected as shown below:

Column 12, line 36, "aliylation" should be --alkylation--

Column 12, line 39, "b 2" should be --2--

Column 12, line 54, "fist" should be --first--

Signed and Sealed this

Twelfth Day of October, 1993

Attest:

BRUCE LEHMAN

Attesting Officer     Commissioner of Patents and Trademarks